(12) United States Patent
Mais et al.

(10) Patent No.: US 6,525,198 B1
(45) Date of Patent: Feb. 25, 2003

(54) METHOD FOR PRODUCING 4,6-DICHLOROPYRIMIDINE WITH SULFUR COMPOUNDS AND PHOSPHORUS COMPOUNDS

(75) Inventors: Franz-Josef Mais, Düsseldorf (DE); Alexander Klausener, Pulheim (DE); Günther Cramm, Leverkusen (DE); Guido Steffan, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/069,089

(22) PCT Filed: Jul. 31, 2000

(86) PCT No.: PCT/EP00/07401
§ 371 (c)(1),
(2), (4) Date: Feb. 7, 2002

(87) PCT Pub. No.: WO01/12610
PCT Pub. Date: Feb. 22, 2001

(30) Foreign Application Priority Data

Aug. 13, 1999 (DE) .......................... 199 38 500

(51) Int. Cl.⁷ ............................ C07D 239/30
(52) U.S. Cl. ..................................... 544/334
(58) Field of Search .......................... 544/334

(56) References Cited

FOREIGN PATENT DOCUMENTS

| EP | 745593 | 12/1996 |
|----|--------|---------|
| WO | 95/29166 | 11/1995 |

OTHER PUBLICATIONS

"Chlorination of Pyrimidines", Research Disclosure, GB, Industrial Opportunities Ltd., Havant, Nr. 391, Nov. 1, 1996, Seiten 690–691, XP000680903, ISSN: 0374-4353 in der Anmeldung erwähnt Beispiel 2.

*Primary Examiner*—John M. Ford
(74) *Attorney, Agent, or Firm*—Godfried R. Akorli

(57) ABSTRACT

The invention relates to a method for the preparation of 4,6-dichloropyrimidine by reacting 4-chloro-6-methoxypyrimidine with at least one sulphur-containing chlorinating agent selected from the group consisting of $SCl_2$, $SOCl_2$, and $SO_2Cl_2$ in the presence of at least one phosphorus compound having the formula $$R_3P=Y_n \qquad (1),$$

in which

R represents $C_1$–$C_{10}$-alkyl or $C_6$–$C_{10}$-aryl, each of which may optionally be substituted by up to five identical or different substituents selected from the group consisting of fluorine, chlorine, bromine, $C_1$–$C_4$-alkyl, and $C_1$–$C_4$-alkoxy, Y represents oxygen or sulphur, and n represents zero or 1.

10 Claims, No Drawings

METHOD FOR PRODUCING 4,6-DICHLOROPYRIMIDINE WITH SULFUR COMPOUNDS AND PHOSPHORUS COMPOUNDS

The present invention relates to a method for the preparation of 4,6-dichloropyrimidine from 4-chloro-6-methoxypyrimidine. 4,6-Dichloropyrimidine is a valuable intermediate for the preparation of crop protection agents.

A number of methods for preparing 4,6-dichloropyrimidine are known starting from 4,6-dihydroxypyrimidine.

It is also known (see Res. Discl. n 391, 690–691 (1996)) that 4,6-dichloropyrimidine can be reacted by reacting 4-chloro-6-methoxypyrimidine with a chlorinating agent of the formula $R_3PCl_2$. The chlorinating agent can be employed as such or be prepared in situ from a compound of the formula $R_3P=O$ and phosgene. It is additionally described therein that 4-chloro-6-methoxypyrimidine does not react with phosphorus oxychloride. The disadvantage of this method is that usually only very incomplete conversion can be achieved and thus 4,6-dichloropyrimidine is obtainable only in low yields and low degrees of purity.

A method for the preparation of 4,6-dichloropyrimidine from 4-chloro-6-methoxypyrimidine has now been found and is characterized in that 4-chloro-6-methoxypyrimidine is reacted with at least one sulphur-containing chlorinating agent selected from the group of $SCl_2$, $SOCl_2$ and $SO_2Cl_2$ and in the presence of at least one phosphorus compound of the formula

$$R_3P=Y_n \qquad (1),$$

in which

R represents $C_1$–$C_{10}$-alkyl or $C_6$–$C_{10}$-aryl, each of which may optionally be substituted by up to 5 identical or different substituents from the group of fluorine, chlorine, bromine, $C_1$–$C_4$-alkyl and $C_1$–$C_4$-alkoxy, Y represents oxygen or sulphur and n represents zero or 1.

Preferred sulphur-containing chlorinating agents are $SOCl_2$ and $SO_2Cl_2$, and preferred phosphorus compounds are triphenylphosphine and triphenylphosphine oxide.

Based on 1 mol of 4-chloro-6-methoxypyrimidine it is possible, for example, to employ at least 1 mol of sulphur-containing chlorinating agent. This amount is preferably 1 to 2 mol.

Based on 1 mol of sulphur-containing chlorinating agent it is possible to employ, for example, 0.01 to 1 mol of phosphorus compounds of the formula (1). This amount is preferably 0.02 to 0.25, particularly preferably 0.05 to 0.1, mol.

The method according to the invention is preferably carried out in the presence of a solvent. Suitable examples are aromatic solvents such as toluene, xylenes, chlorobenzene, dichlorobenzenes, chlorotoluenes, benzonitrile and benzotrifluoride, nitrogen-containing solvents such as N-methylpyrrolidone, dimethylformamide, dimethylacetamide and cyclic ureas and oxygen-containing solvents such as ethers, in particular higher-boiling ethers and polyethers. It is also possible to employ mixtures of solvents.

The method according to the invention can be carried out, for example, at temperatures in the range from 50 to 200° C. 75 to 175° C. are preferred, especially 100 to 150° C.

The pressure is in principle not critical. Only if it is wished to employ solvents which boil below the desired reaction temperature at atmospheric pressure is it indicated to operate under elevated pressure so that the solvent is present at least partly in liquid form.

On the assumption that, at the given temperature, no precursors, products and solvents escape from the reaction vessel, the pressure can be, for example, in the range from 0.1 to 5 bar. The pressure is preferably atmospheric, particularly preferably using a solvent which boils under reflux at the required reaction temperature under atmospheric pressure.

The method of the invention can be carried out batchwise and continuously.

In a preferred embodiment of the method according to the invention, 4-chloro-6-methoxypyrimidine, the phosphorus compound and a solvent are mixed, the mixture is heated to the reaction temperature, and then the sulphur-containing chlorinating agent is metered in, where appropriate in a plurality of portions.

The reaction mixture present after the reaction can be worked up, for example, by distilling it through a column, where appropriate under reduced pressure.

It is possible with the method according to the invention to convert 4-chloro-6-methoxypyrimidine into 4,6-dichloropyrimidine in a simple manner. The conversion takes place virtually completely, in contrast to the prior art. This makes it possible to prepare a product with a high 4,6-dichloropyrimidine content in a simple manner. This is desirable because unreacted 4-chloro-6-methoxypyrimidine can be removed only with difficulty by distillation.

EXAMPLES

Example 1

29.0 g of 4-chloro-6-methoxypyrimidine and 5.6 g of triphenylphosphine oxide were introduced into 150 g of chlorobenzene and heated to 140° C. with stirring. 35.7 g of thionyl chloride were added dropwise to this solution over the course of 1 hour. The mixture was then stirred at 140° C. After 6 hours, a further 11.9 g of thionyl chloride were added dropwise, and then stirring was continued for 6 hours. This was followed by cooling to 25° C. A final weight of 304.1 g was obtained. HPLC analysis showed a 4,6-dichloropyrimidine content of 9.34% (which corresponds to a yield of 95.3% of theory). The reaction mixture contained only 0.1% 4-chloro-6-methoxypyrimidine (which corresponds to 1.05% of the starting material).

Example 2

Example 1 was repeated, but 200 ml of a mixture of isomeric xylenes were employed in place of chlorobenzene, operating at 135° C. HPLC analysis showed a 4,6-dichloropyrimidine yield of 93.6% and unreacted 4-chloro-6-methoxypyrimidine in an amount of 2.6% of the starting material.

Example 3

Example 1 was repeated but 49.2 g of a mixture of 3 moles of $SOCl_2$ and 1 mole of $SO_2Cl_2$, in place of thionyl chloride were added dropwise over the course of 1 hour and, after 6 hours, no further chlorinating agent was added. HPLC analysis showed a 4,6-dichloropyrimidine yield of 89.3% of theory.

What is claimed is:

1. A method for the preparation of 4,6-dichloropyrimidine from 4-chloro-6-methoxypyrimidine comprising reacting 4-chloro-6-methoxypyrimidine with at least one sulphur-containing chlorinating agent selected from the group consisting of $SCl_2$, $SOCl_2$, and $SO_2Cl_2$ in the presence of at least one phosphorus compound having the formula

 (1), in which

R represents $C_1$–$C_{10}$-alkyl or $C_6$–$C_{10}$-aryl, each of which may optionally be substituted by up to five identical or different substituents selected from the group consisting of fluorine, chlorine, bromine, $C_1$–$C_4$-alkyl, and $C_1$–$C_4$-alkoxy, Y represents oxygen or sulphur, and n represents zero or 1.

2. A method according to claim 1 wherein the sulphur-containing chlorinating agent is $SOCl_2$ and/or $SO_2Cl_2$.

3. A method according to claim 1 wherein the phosphorus compound is triphenylphosphine and/or triphenylphosphine oxide.

4. A method according to claim 1 wherein at least 1 mol of the sulphur-containing chlorinating agent is used per 1 mol of 4-chloro-6-methoxypyrimidine.

5. A method according to claim 1 wherein 0.01 to 1 mol of the phosphorus compound is used per 1 mol of the sulphur-containing chlorinating agent.

6. A method according to claim 1 carried out in the presence of an aliphatic solvent, an aromatic solvent, a nitrile, a nitrogen-containing solvent, an ether, an oxygen-containing solvent, or a mixture thereof.

7. A method according to claim 5 wherein the aromatic solvent is toluene, a xylene, chlorobenzene, a dichlorobenzene, a chlorotoluene, benzonitrile, benzotrifluoride, or a mixture thereof.

8. A method according to claim 6 wherein the nitrogen-containing solvent is N-methylpyrrolidone, dimethylformamide, dimethylacetamide, or a cyclic urea or a mixture thereof.

9. A method according to claim 6 wherein the oxygen-containing solvent is a polyether or a mixture of polyethers.

10. A method according to claim 1 carried out at from 50 to 200° C.

* * * * *